(12) United States Patent
Andersson et al.

(10) Patent No.: US 6,595,205 B2
(45) Date of Patent: Jul. 22, 2003

(54) INHALATION DEVICE

(75) Inventors: Malin Andersson, Stockholm (SE); Maria Benktzon, Sollentuna (SE); Lennart Brunnberg, Tyresö (SE); Sven-Eric Juhlin, Stockholm (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/074,007

(22) Filed: Feb. 14, 2002

(65) Prior Publication Data

US 2002/0073992 A1 Jun. 20, 2002

Related U.S. Application Data

(63) Continuation of application No. 09/331,904, filed as application No. PCT/SE99/00502 on Mar. 26, 1999, now abandoned.

(30) Foreign Application Priority Data

Mar. 27, 1998 (SE) ............................................... 9801078
Mar. 26, 1999 (WO) ............................... PCT/SE99/00502

(51) Int. Cl.$^7$ ............................................. A61M 11/00
(52) U.S. Cl. ............................. 128/200.23; 128/203.23
(58) Field of Search ....................... 128/200.14, 200.23, 128/203.12, 203.15, 203.19, 203.23

(56) References Cited

U.S. PATENT DOCUMENTS

| | | |
|---|---|---|
| 3,456,644 A | 7/1969 | Thiel |
| 3,456,645 A | 7/1969 | Brock |
| 3,565,070 A | 2/1971 | Hanson et al. |
| 3,636,949 A | 1/1972 | Kropp |
| 3,789,843 A | 2/1974 | Armstrong et al. |
| 3,826,413 A | 7/1974 | Warren |
| 4,648,393 A | 3/1987 | Landis et al. |
| 4,678,106 A | 7/1987 | Newell et al. |
| 4,834,083 A | 5/1989 | Byram et al. |
| 5,027,808 A | 7/1991 | Rich et al. |
| 5,031,610 A | 7/1991 | Armstrong et al. |
| 5,059,204 A | 10/1991 | Lawson et al. |
| 5,060,643 A | 10/1991 | Rich et al. |
| 5,119,806 A | 6/1992 | Palson et al. |
| 5,217,004 A | 6/1993 | Blasnik et al. |
| 5,224,472 A | 7/1993 | Pesenti et al. |
| 5,408,994 A | 4/1995 | Wass et al. |
| 5,447,150 A | 9/1995 | Bacon |
| 5,511,540 A | 4/1996 | Bryant et al. |
| 5,692,492 A | 12/1997 | Bruna et al. |
| 6,029,662 A | 2/2000 | Marcon |

FOREIGN PATENT DOCUMENTS

| | | |
|---|---|---|
| EP | 0123456 A2 | 1/2000 |
| WO | 94/19040 | 9/1994 |

*Primary Examiner*—Weilun Lo
*Assistant Examiner*—Mital Patel
(74) *Attorney, Agent, or Firm*—Nixon & Vanderhye

(57) ABSTRACT

An actuator for an inhaler for delivering medicament by inhalation, comprising: a housing (22) which defines a cavity (34) for receiving a canister (8) which comprises a body (10) which defines a chamber containing medicament and a valve stem (13) which extends from the body (10), the body (10) and the valve stem (13) of the canister (8) being relatively movable between a first, non-actuated position in which the canister (8) is closed and a second, actuated position in which the canister (8) is open; a nozzle block (24) for receiving the valve stem (13) of the canister (8); a mouthpiece (21) for providing medicament from the nozzle block (24) to the mouth of a user; a locking mechanism (16) for selectively locking the canister (8) in the non-actuated position, which locking mechanism (16) when released allows for the actuation of the canister (8); and a loading mechanism (18) which comprises a biasing element (134) for loading one of the body (10) or the valve stem (13) of the canister (8) with an actuating force for actuating the same and a lever arm (132) which is pivotally coupled to the housing (22) for loading the biasing element (134) when rotated in one sense, which lever arm (132) is configured so as to be rotated in the one sense on the manual application of opposed forces substantially orthogonal to the longitudinal axis of the canister (8).

21 Claims, 6 Drawing Sheets

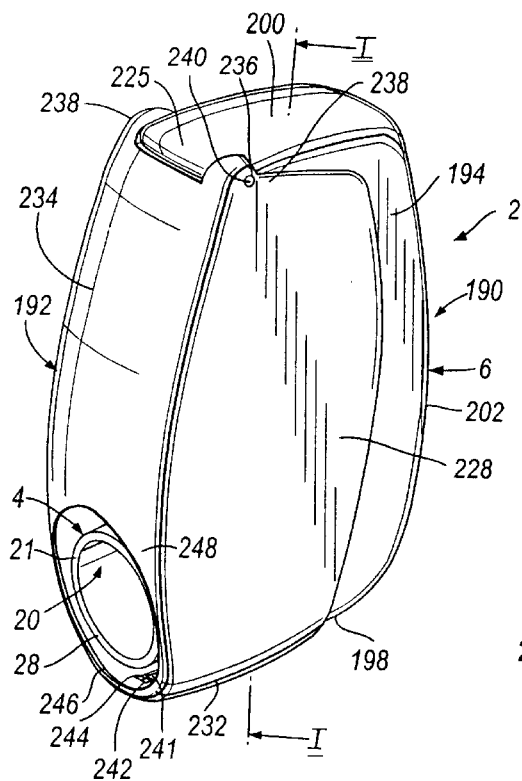
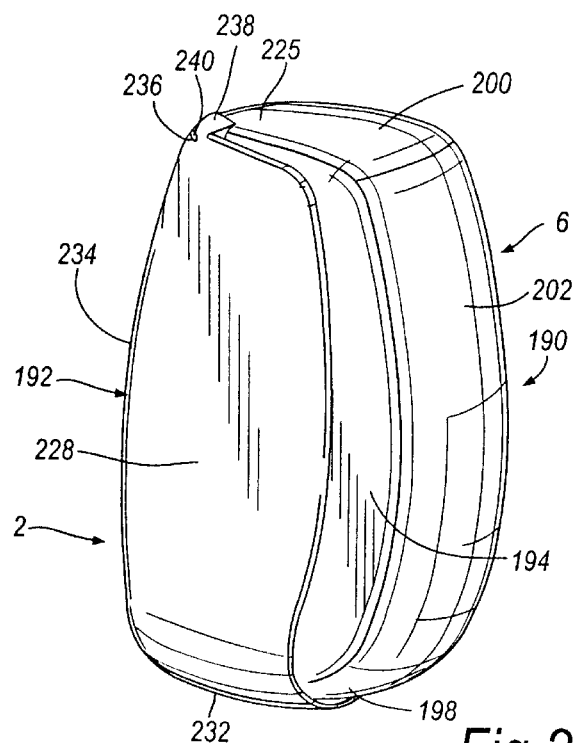

INHALATION DEVICE

This application is a continuation of U.S. Ser. No. 09/331,904 filed Jun. 29, 1999, now abandoned, which is a national stage entry under 35 U.S.C. 371 of PCT/SE99/00502, filed Mar. 26, 1999.

The present invention relates to an actuator for an inhaler for administering medicament by inhalation and to an inhaler, particularly a breath-actuated inhaler, including the same.

BACKGROUND OF THE INVENTION

Breath-actuated inhalers are well known for delivering metered doses of medicament from aerosol canisters of the kind which comprise a body which defines a chamber containing medicament in a propellant under pressure, a valve stem which extends axially from one end of the body and an internal metering valve which is normally biased to a closed position and opened to deliver a metered dose of medicament when the valve stem is depressed. Such inhalers include a locking mechanism for selectively locking a canister in a non-actuated position and a loading mechanism for loading the canister with an actuation force, with the locking mechanism being released on inhalation by a user such that the loading mechanism actuates the canister to deliver a metered dose of medicament.

Examples of known breath-actuated inhalers are disclosed in U.S. Pat. No. 4,648,393, U.S. Pat. No. 5,060,643, U.S. Pat. No. 5,119,806 and WO-A-94/19040. U.S. Pat. No. 4,648,393 discloses an inhaler in which a biasing element for actuating a canister is loaded by pulling on one end of a lever arm. U.S. Pat. No. 5,060,643 discloses an inhaler in which a biasing element for actuating a canister is loaded by acting on a cap which is displaceable along the longitudinal axis of the canister. U.S. Pat. No. 5,119,806 discloses an inhaler in which a biasing element for actuating a canister is loaded by pulling on a strap. WO-A-94/19040 discloses an inhaler in which a biasing element for actuating a canister is loaded in lifting part of the casing so as to expose the mouthpiece.

SUMMARY OF THE INVENTION

It is an aim of the present invention to provide an actuator for an inhaler for administering medicament by inhalation which can be loaded in a quick and easy manner.

Accordingly, the present invention provides an actuator for an inhaler for delivering medicament by inhalation, comprising: a housing which defines a cavity for receiving a canister which comprises a body which defines a chamber containing medicament and a valve stem which extends from the body, the body and the valve stem of the canister being relatively movable between a first, non-actuated position in which the canister is closed and a second, actuated position in which the canister is open; a nozzle block for receiving the valve stem of the canister; a mouthpiece for providing medicament from the nozzle block to the mouth of a user, a locking mechanism for selectively locking the canister in the non-actuated position, which locking mechanism when released allows for the actuation of the canister; and a loading mechanism which comprises a biasing element for loading one of the body or the valve stem of the canister with an actuating force for to actuating the same and a lever arm which is pivotally coupled to the housing for loading the biasing element when rotated in one sense, which lever arm is configured so as to be rotated in the one sense on the manual application of opposed forces substantially orthogonal to the longitudinal axis of the canister.

Preferably, the loading mechanism further comprises a drawbar which is movably disposed relative to the pivot of the lever arm and coupled to the biasing element such that the drawbar is loaded as the biasing element is loaded, which drawbar includes at least one catch through which the biasing element is coupled to the one of the body or the valve stem of the canister.

More preferably, the biasing element is coupled to the lever arm at a point spaced from the pivot thereof.

Preferably, the pivot of the lever arm comprises a hinge pin and the drawbar includes at least one elongate slot through which the hinge pin extends such that the drawbar is moveably disposed to the housing between a first position and a second, extended position.

More preferably, the loading mechanism further comprises a support member which is pivotally coupled to the drawbar and pivotally and slideably coupled to the lever arm such that the drawbar is moved to the extended position when the lever arm is rotated in the other sense.

Yet more preferably, the drawbar includes a projection which is configured to engage the canister when rotated in the other sense so as to draw the canister at least partially from the cavity defined by the housing.

Preferably, the locking mechanism comprises a movable flap member which is configured to move on inhalation by a user through the mouthpiece and a link assembly which is operably coupled to the flap member such as to be released from a locking position in which the canister is locked in the non-actuated position on movement of the flap member.

More preferably, the link assembly comprises a first link which is pivotally coupled to the housing and includes an engagement surface which, in the locking position, is configured to prevent relative movement of the body and the valve stem of the canister, a second link which is pivotally coupled to the first link and operably coupled to the flap member and a biasing element for biasing the first link to the locking position.

Yet more preferably, when the first link is in the locking position, the engagement surface of the first link extends into the cavity defined by the housing such as to be engageable by the canister.

Preferably, when the first link is in the locking position, the engagement surface of the first link extends substantially orthogonally to the longitudinal axis of the canister.

Preferably, the first link and the housing are configured such that the first link cannot be rotated beyond the locking position under the action of the biasing element.

Preferably, the first link further includes a further engagement surface which is configured to engage a surface of the canister when in the actuated position and hold the first link in a displaced position.

Preferably, the flap member includes an axle and the second link includes a catch surface which is configured to engage the axle in the locking position and be disengaged therefrom on movement of the flap member by inhalation.

More preferably, the second link includes an engagement surface and the flap member includes a lever member, which engagement surface and lever member are configured such that, on movement of the flap member by inhalation, the lever member engages the engagement surface such as to move the second link and disengage the catch surface thereof from the axle of the flap member.

Yet more preferably, the engagement surface of the second link and the lever member are further configured such that the flap member is disposed in the closed position when the locking mechanism is in the locking position.

Preferably, the second link includes a further engagement surface which together with the lever member of the flap member is configured to hold the flap member in the open position when the locking assembly is in the displaced position.

Preferably, the actuator further comprises a casing which comprises first and second casing parts which are pivotally coupled between a first, closed position and a second, open position.

More preferably, the housing is fixed to one of the first and second casing parts and the other of the first and second casing parts is configured, on movement of the first and second casing parts between the closed and open positions, to rotate the lever arm in the one sense such as to load the biasing element.

Yet more preferably, the other of the first and second casing parts includes an opening through which the mouthpiece extends in the open position of the casing parts.

Preferably, the casing further comprises a latch for holding the casing parts in the open position.

Preferably, the pivot of the lever arm is substantially orthogonal to the longitudinal axis of the canister.

Such an actuator advantageously provides that the loading mechanism can be loaded in a single-handed operation without requiring any re-positioning of the hand in picking up the inhaler and bringing the same to the mouth. Indeed, the actuator is such as not to require any particular dexterity on the part of the user and can be operated, for example, by a user with limited hand function or when wearing gloves.

The present invention also provides an inhaler comprising the above-described actuator and a canister containing medicament.

BRIEF DESCRIPTION OF THE DRAWINGS

A preferred embodiment of the present invention will now be described hereinbelow by way of example only with reference to the accompanying drawings, in which:

FIG. 1 illustrates a front perspective view of a breath-actuated inhaler in accordance with a preferred embodiment of the present invention in the closed configuration;

FIG. 2 illustrates a rear perspective view of the inhaler of FIG. 1 in the closed configuration;

DETAILED DESCRIPTION OF PREFERRED EMBODIMENTS

Figure 3:
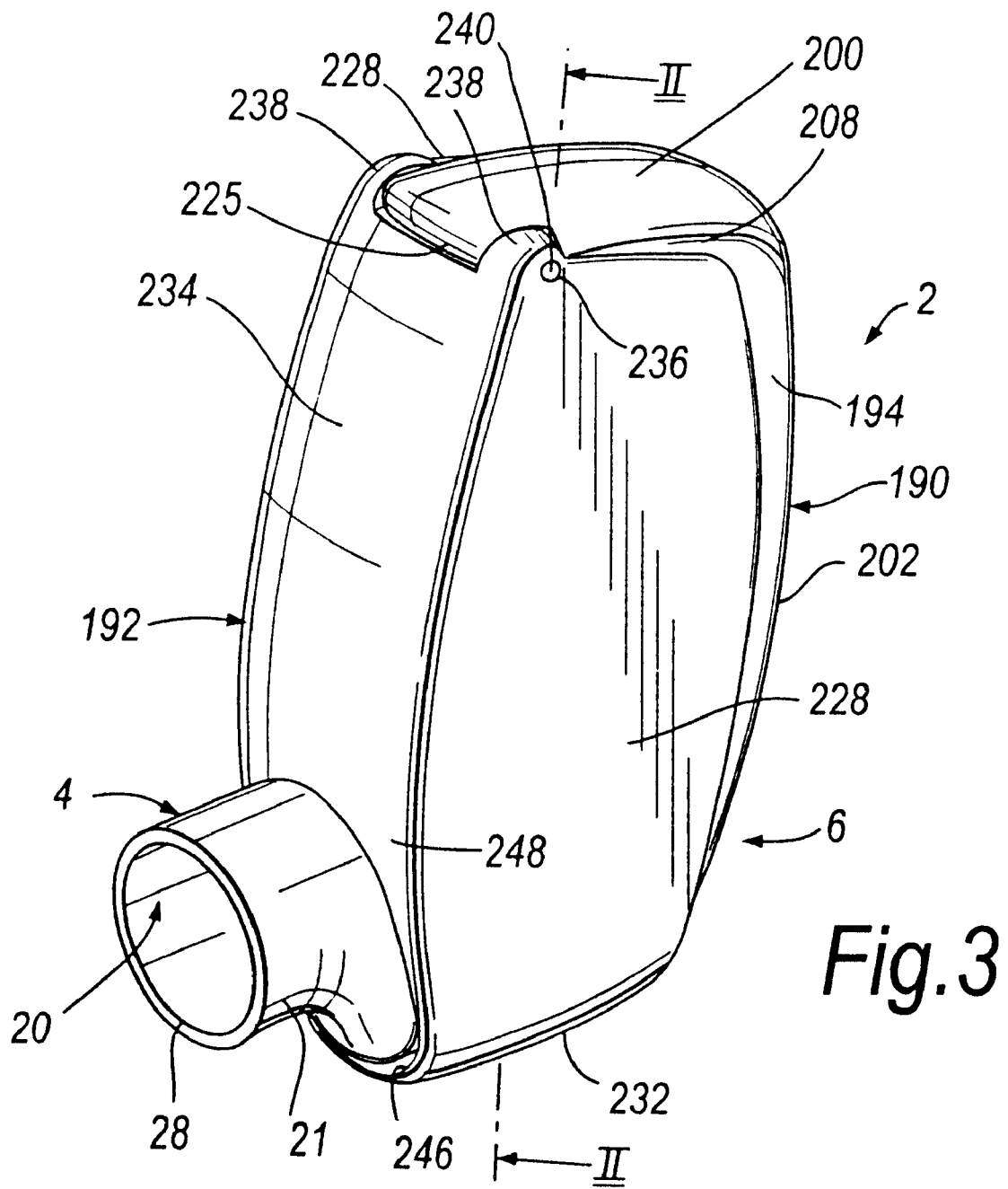
FIG. 3 illustrates a front perspective view of the inhaler of FIG. 1 in the open configuration.
Figure 4:
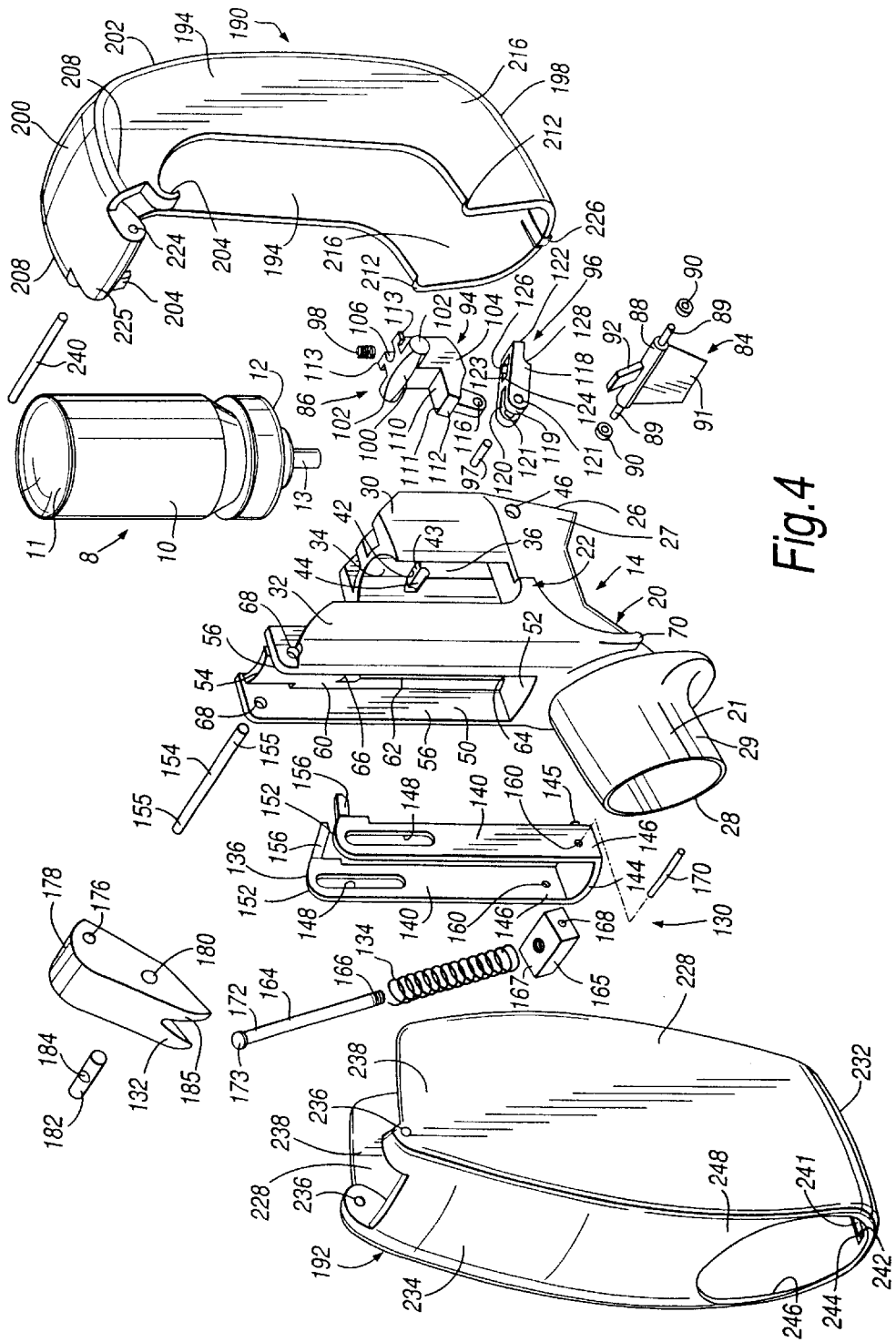
FIG. 4 illustrates an exploded perspective view of the inhaler of FIG. 1.

The inhaler comprises an actuator 2 which comprises a delivery unit 4 and a casing 6 within which the delivery unit 4 is removably disposed and an aerosol canister 8 which is fitted in the delivery unit 4. The aerosol canister 8 comprises a body 10 which defines a chamber containing medicament in a propellant under pressure, one end 11 of the body 10 defining the base of the canister 8 and the other end 12 of the body 10 defining the head of the canister 8, a valve stem 13 which extends axially from the head end 12 of the body 10 and an internal metering valve (not illustrated) which is normally biased to a closed position and opened to deliver a metered dose of medicament from the canister 8 when the valve stem 13 is depressed.

The delivery unit 4 comprises a main body 14 for receiving the canister 8, a locking mechanism 16 for selectively locking the canister 8 in a non-actuated position and a loading mechanism 18 for loading the body 10 of the canister 8 with a predetermined actuation force for actuating the same.

The main body 14 comprises a shaped tubular section 20, a part of which defines a mouthpiece 21 which is in use gripped in the lips of a user, a housing 22 in which the canister 8 is in use fitted and a nozzle block 24 for receiving the valve stem 13 of the canister 8 and delivering medicament to the mouthpiece 21. In this embodiment the main body 14 is formed as a single integral unit.

The tubular section 20, which in part defines the mouthpiece 21, extends substantially laterally beneath the housing 22 and includes a first, inlet opening 26 at one, the rear, end 27 thereof through which air is in use inhaled and a second, outlet opening 28 at the other, forward, end 29 thereof through which air drawn through the inlet opening 26 and propellant containing medicament delivered from the canister 8 is in use inhaled.

The housing 22 comprises first and second opposed body sections 30, 32 which together define a cavity 34, in this embodiment of substantially circular section, in which the canister 8 is removably housed.

The first body section 30 is disposed above the rear end 27 of the tubular section 20 and is configured to support the component parts of the locking mechanism 16 as will be described in more detail hereinbelow. The first body section 30 includes a through slot 36 which extends along the longitudinal extent thereof, one, the lower, end 38 of the through slot 36 being open and extending into the tubular section 20 and the other, upper, end 40 of the through slot 36 being closed. The through slot 36 includes opposed lateral sections 42, 42 at the upper end 40 thereof, each lateral section 42 including one, the lower, surface 43 which includes a part-cylindrical bearing surface 44, in this embodiment semi-cylindrical in section. The first body section 30 further includes opposed through holes 46, 46 disposed laterally adjacent the lower end 38 of the through slot 36.

The second body section 32 is disposed forward of the first body section 30 relative to the longitudinal extent of the tubular section 20 and is of greater length than the first body section 30. The second body section 32 includes a channel 50 which extends along the longitudinal extent thereof, one, the lower, end 52 of the channel 50 being closed and the other, upper, end 54 of the channel 50 being open. In this embodiment the channel 50 is of substantially rectangular section and includes opposed side walls 56, 56 and a base wall 60 which interconnects the same. The channel 50 further includes a through slot 62 in the base wall 60 thereof, one, the lower, end 64 of the through slot 62 extending from the lower end 52 of the channel 50 and the other, upper, end 66 of the through slot 62 being closed. The second body section 32 still further includes opposed through holes 68, 68 in the side walls 56, 56 at the upper end 54 of the channel 50. The second body section 32 also further includes oppositely-directed laterally-extending projections 70, 70 by which the delivery unit 4 is clipped to the casing 6.

The nozzle block 24 includes a tubular bore 72 for receiving the valve stem 13 of the canister 8 which is co-axial with the longitudinal axis of the housing 22. The tubular bore 72 is open at one, the upper, end 74 thereof and includes an upper part 76 having an internal dimension substantially the same as the outer dimension of the valve stem 13 of the canister 8 and a lower part 78 having a smaller internal dimension, which parts 76, 78 together define an annular seat 80 for the distal end of the valve stem 13. The tubular bore 72 further includes a laterally-directed spray orifice 82 in the lower part 78 thereof which is configured to direct a spray into and through the tubular section 20 defining in part the mouthpiece 21.

The locking mechanism 16 comprises a rotatable flap member 84 which is configured to be rotated on inhalation by a user and a link assembly 86 which is operably coupled to the flap member 84 between a first, inward locking position which is such as to prevent the actuation of the canister 8 and a second, outward displaced position which allows the loading mechanism 18 to actuate the canister 8.

Figure 5:
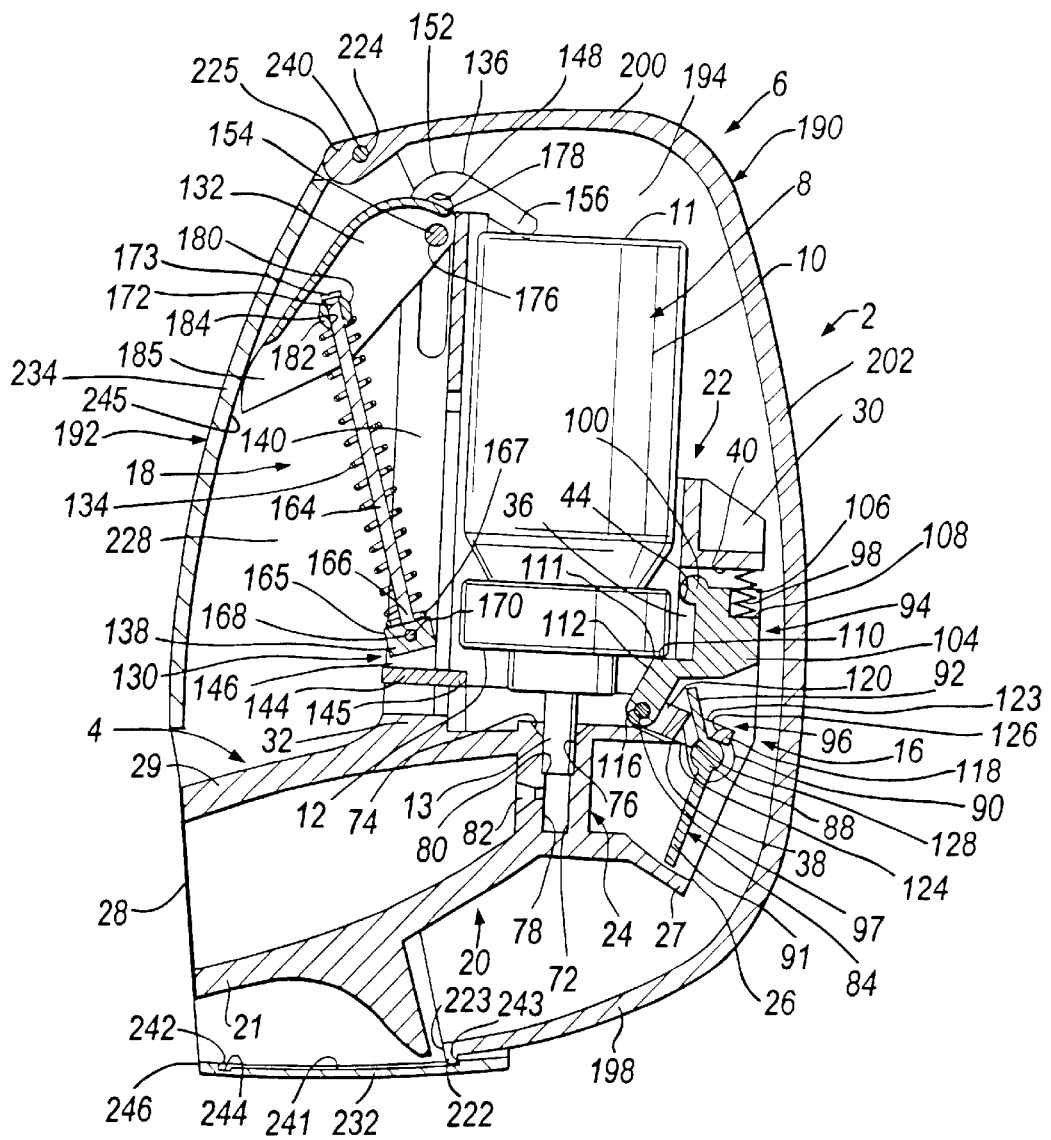
FIG. 5 illustrates a vertical sectional view along section I—I in FIG. 1.
Figure 6:
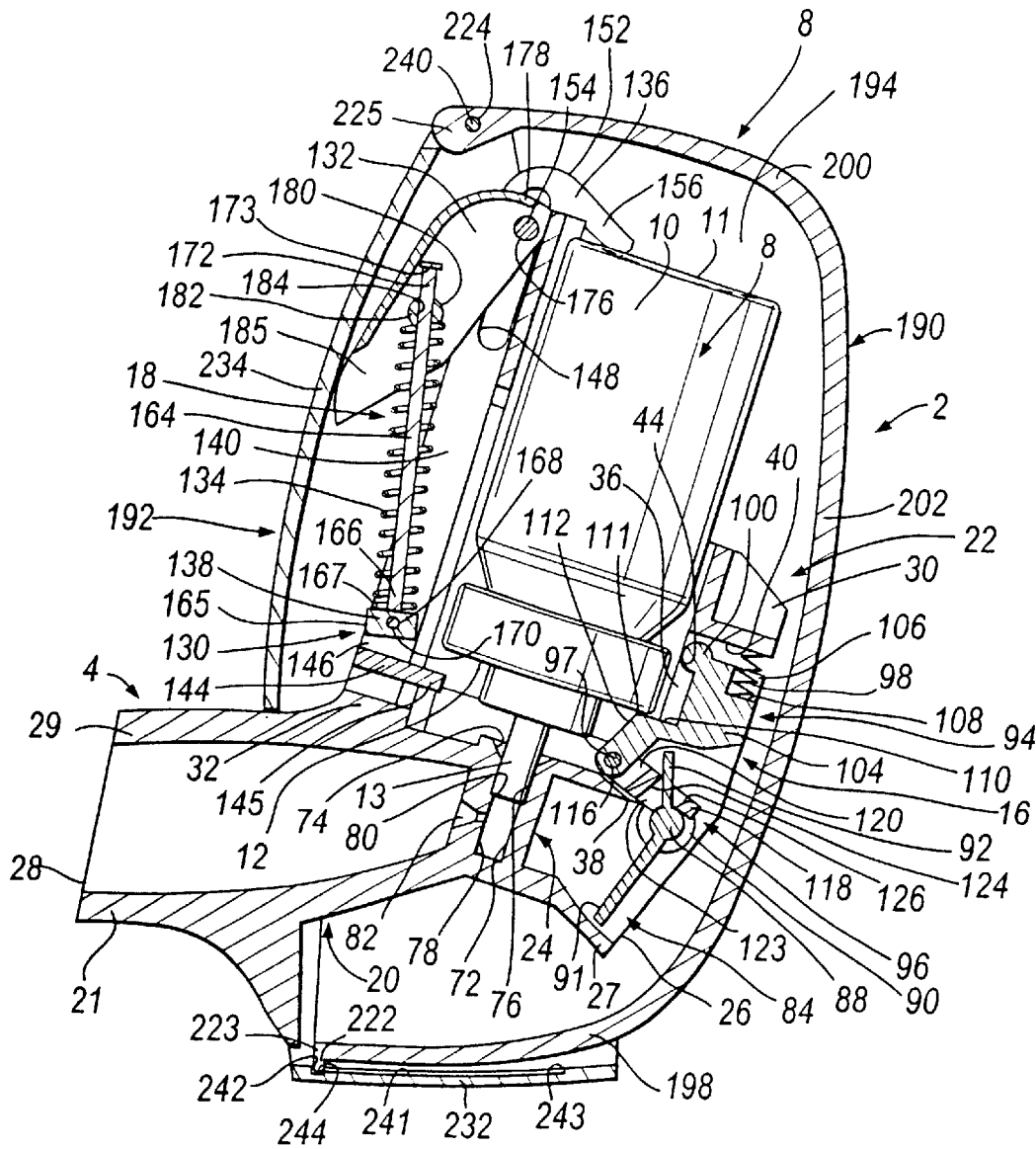
FIG. 6 illustrates a vertical sectional view along section II—II in FIG. 3, with the inhaler in the non-actuated position.
Figure 7:
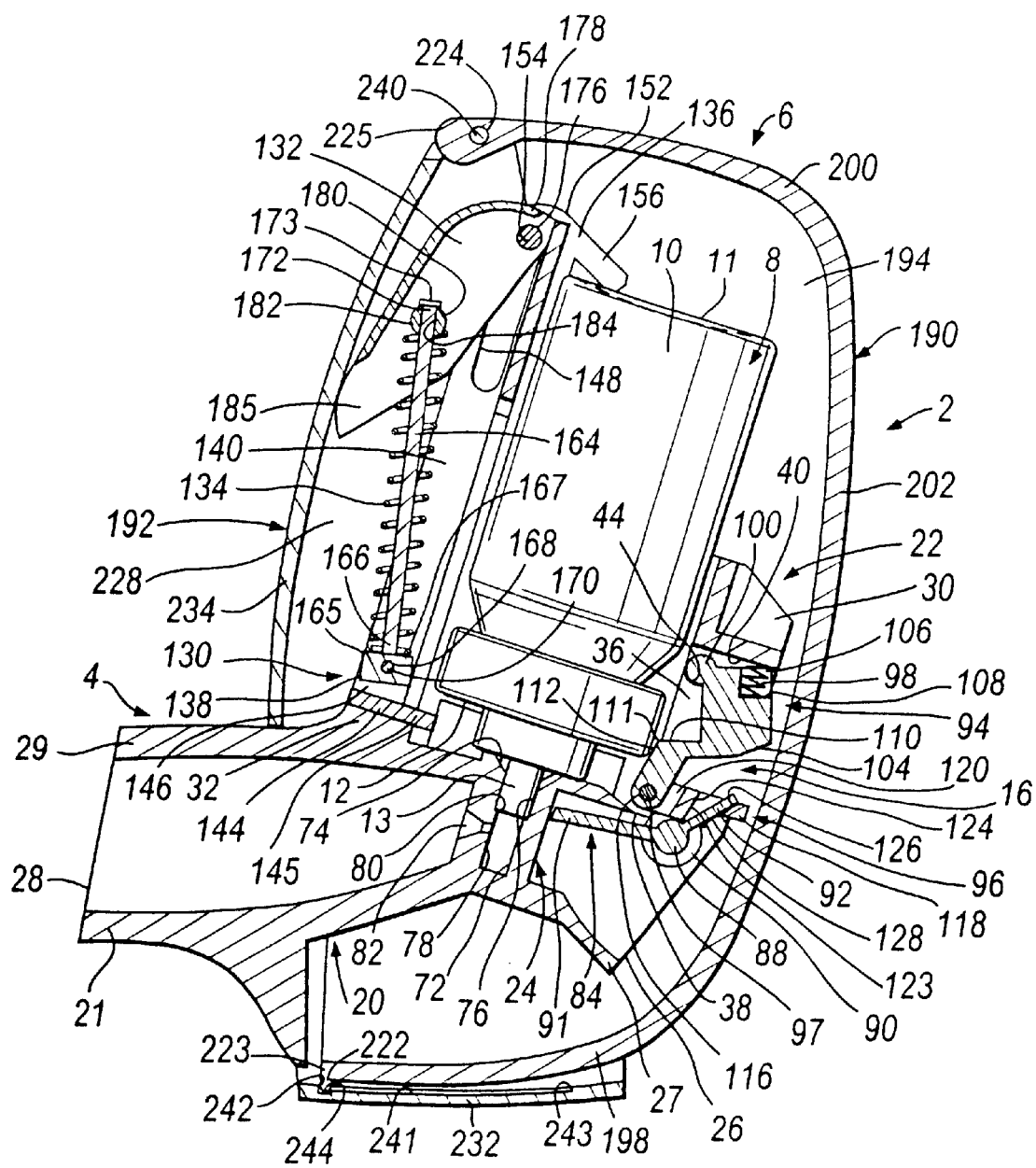
FIG. 7 illustrates a vertical sectional view along section II—II in FIG. 3, with the inhaler in the actuated position.

The flap member 84 comprises an axle 88, the opposed ends 89, 89 of which are located in bushes 90, 90 which are disposed in the lateral openings 46, 46 in the first body section 30 of the housing 22 and act as pivots, a vane 91 which extends radially from the axle 88 and a lever member 92 which extends radially from a mid-point of the axle 88 in a direction substantially opposite the vane 91. The flap member 84 is configured to be rotatable between a first, closed position (FIGS. 5 and 6) in which the vane 91 substantially closes the inlet opening 26 of the tubular section 20 and a second, open position (FIG. 7) in which the vane 91 is raised and allows air to be drawn through the tubular section 20.

The link assembly 86 comprises first and second links 94, 96 which are pivotally coupled about a hinge pin 97, with the first link 94 being pivotally coupled to the first body section 30 of the housing 22 and the second link 96 being operably coupled to the lever member 92 of the flap member 84, and a biasing element 98, in this embodiment a compression spring, for biasing the first and second links 94, 96 to the inward locking position.

The first link 94 comprises an axle 100, the opposed ends 102, 102 of which are located in the bearing surfaces 44, 44 in the lower surfaces 43, 43 of the lateral extensions 42, 42 of the through slot 36 in the first body section 30, and a body member 104 which is configured so as to be rotatably disposed within the through slot 36. The body member 104 includes a cavity 106 which receives one end of the biasing element 98 and includes a surface 108 which acts as a bearing surface, the biasing element 98 being disposed between the bearing surface 108 and the closed end 40 of the through slot 36 in the first body section 30 such as to bias the body member 104 inwardly into the cavity 34 defined by the housing 22. The body member 104 also includes a first engagement surface 110 which is spaced radially from and directed substantially tangentially to the pivot of the axle 100, which first engagement surface 110 includes a free edge 111 which, in the inward locking position of the first link 94, is disposed in the cavity 34 defined by the housing 22 such that the first engagement surface 110 presents a surface which is substantially orthogonal to the longitudinal axis of the cavity 34 and engages the head end 12 of the body 10 of the canister 8 so as to prevent downward movement of the same. The first engagement surface 110 is disposed such that, when the first link 94 is in the inward locking position, the body 10 of the canister 8 is held a predetermined distance from the annular seat 80 in the tubular bore 72 of the nozzle block 24, in which non-actuated position the metering valve of the canister 8 is closed. The body member 104 further includes a second engagement surface 112 which, in this embodiment, extends from the inwardly-directed free edge 111 of the first engagement surface 110 in a substantially radial direction relative to the pivot of the axle 100, which second engagement surface 112, in the actuated position of the canister 8, is configured to abut a side surface of the body 10 of the canister 8 such as to hold the first link 94 in the outward displaced position and thereby hold the flap member 84 in the open position. The body member 104 still further includes oppositely-directed lateral projections 113, 113 which act to limit the extent to which the body member 104 extends into the cavity 34 defined by the housing 22. In this embodiment the lateral projections 113, 113 are configured to engage the respective lower surfaces 43, 43 of the lateral extensions 42, 42 of the through slot 36 in the first body section 30 with the first engagement surface 110 directed substantially orthogonally to the longitudinal axis of the cavity 34 defined by the housing 22. The body member 104 yet further includes a through hole 116 for receiving the hinge pin 97, which through hole 116 defines the pivot between the first and second links 94, 96 and is disposed radially further from the pivot of the axle 100 than the first engagement surface 110.

The second link 96 comprises an elongate body member 118 which is configured to ride on the axle 88 of the flap member 84, one end 119 of which body member 118 includes a first through slot 120 which receives a part of the body member 104 of the first link 94 and opposed lateral openings 121, 121 through which extends the hinge pin 97 and the other end 122 of which body member 118 includes a second, enclosed through slot 123 in which the lever member 92 of the flap member 84 is captively disposed, one end 124 of which second through slot 123 is adjacent and the other end 126 of which second through slot 123 is remote from the one end 119 of the body member 118. The body member 118 further includes a catch surface 128, in this embodiment a curved surface of the same sectional shape as the axle 88 of the flap member 84, which, in the inward locking position of the link assembly 86, engages the axle 88 such as to support the second link 96 and hence in turn the first link 94.

Operation of the locking assembly 16 is as follows. When a user inhales through the mouthpiece 21, the vane 91 of the flap member 84 is acted upon such that the flap member 84 is rotated inwardly and upwardly. This rotation of the flap member 84 causes the lever member 92 thereof to rotate, which lever member 92 in engaging the other end 126 of the second through slot 123 in the body member 118 of the second link 96 draws the second link 96 outwardly and upwardly such that the catch surface 128 of the body member 118 clears the axle 88 of the flap member 84 sufficiently that, when the canister 8 is loaded by the loading mechanism 18, the second link 96 is driven outwardly by the loaded first link 94 and the link assembly 86 assumes the outward displaced position. In this displaced position, the second link 96, as a result of the engagement of the one end 124 of the second through slot 123 in the body member 118 with the lever member 92 of the flap member 84, holds the flap member 84 in the open position. While the body 10 of the canister 8 remains loaded, the first and second links 94, 96 of the link assembly 86 remain in the displaced position as the first link 94 is unable to return to the locking position because of the second engagement surface 112 of the body member 104 thereof abutting the side surface of the body 10 of the canister 8. When the body 10 of the canister 8 is unloaded and returned to the closed position by the closure spring in the metering valve thereof, the first link 94 under the action of the biasing element 98 returns to the locking position, in so doing drawing the coupled second link 96 inwardly, which in turn draws the flap member 84 to the closed position as a result of the engagement between the other end 126 of the second through slot 123 in the body member 118 of the second link 96 and the lever member 92 of the flap member 84. When returned to this locking position the catch surface 128 on the body member 118 of the second link 96 is again located against the axle 88 of the flap member 84.

The loading mechanism 18 comprises a drawbar assembly 130 which is slideably disposed to the housing 22, a lever arm 132 which is pivotally coupled to the housing 22 and a biasing element 134, in this embodiment a compression spring, which is disposed between the drawbar assembly 130 and the lever arm 132 such as to load the drawbar assembly 130 on acting upon the lever arm 132.

The drawbar assembly 130 comprises a drawbar 136 which is slideably disposed in the channel 50 in the second body section 32 of the housing 22 and a support member 138 for supporting the biasing element 134. The drawbar 136 comprises opposed elongate members 140, 140 which are of the same length as the channel 50 in the second body section 32 of the housing 22 and configured to slide adjacent the side walls 56, 56 of the channel 50 and a web member 144 which interconnects one, the lower, ends 146, 146 of the elongate members 140, 140. In this embodiment the web member 144 includes an inwardly-directed projection 145 which projects through the through slot 62 in the base wall 60 of the channel 50 such as to engage the head end 12 of the body 10 of the canister 8 when slid upwardly through the through slot 62. The elongate members 140, 140 include opposed elongate through slots 148, 148 at the other, upper, ends 152, 152 thereof through which extend a hinge pin 154 which extends through the lateral openings 68, 68 in the side walls 56, 56 of the channel 50 in the housing 22, which hinge pin 154 is of such length that the opposed ends 155, 155 thereof extend beyond the lateral openings 68, 68 in the side walls 56, 56 of the channel 50. With this configuration, the drawbar 136 is slideable between a first, lowered position in which the drawbar 136 is disposed within the channel 50 and a second, raised position in which the drawbar 136 extends partially from the channel 50. In this second, raised position the canister 8 is lifted partially out of the housing 22 by virtue of the engagement of the projection 145 of the web member 144 of the drawbar 136 with the head end 12 of the body 10 of the canister 8 and provides for easy replacement of the canister 8. The elongate members 140, 140 further include inwardly-directed projections 156, 156 at the upper ends 152, 152 thereof, which projections 156, 156 are configured to engage the base end 11 of the body 10 of the canister 8. The elongate members 140, 140 yet further include opposed through holes 160, 160 at the lower ends 152, 152 thereof. The support member 138 comprises an elongate bar 164 and a support block 165 which is fitted, for example, by screw fitting, to one, the lower, end 166 of the elongate bar 164. The support block 165 includes a bearing surface 167 for one end of the biasing element 134 and a through hole 168 through which extends a hinge pin 170 which extends through the opposed through holes 160, 160 in the elongate members 140, 140 of the drawbar 136 and about which the support member 138 is rotatable. The other, upper end 172 of the elongate bar 164 includes an enlarged head 173.

The lever arm 132 includes a first through hole 176 at one end 178 thereof through which extends the hinge pin 154 which extends through the through holes 68, 68 in the opposed side walls 56, 56 of the channel 50 in the first body section 30 and about which the lever arm 132 is rotatable. The lever arm 132 further includes a second through hole 180 which is spaced from the first through hole 176 and through which extends a hinge pin 182. The hinge pin 182 includes a transverse through hole 184 through which extends the other end 172 of the elongate bar 164 of the support member 138, with the hinge pin 182 acting as a bearing surface for the other end of the biasing element 134 and the elongate bar 164 being captively disposed thereto by the enlarged head 173 thereof. The other, free end 185 of the lever arm 132 is acted upon to load the loading mechanism 18 as will be described further hereinbelow.

Operation of the loading mechanism 18 is as follows. In applying a force to the free end 185 of the lever arm 132, the lever arm 132 is rotated about the hinge pin 154 and a load is applied to the biasing element 134. As the biasing element 134 is progressively loaded, with the body 10 of the canister 8 fixed in position by the locking mechanism 16, any space between the projections 156 on the elongate members 140, 140 of the drawbar 136 and the base end 11 of the body 10 of the canister 8 is taken up such that the projections 156, 156 abut the base end 11 of the body 10 of the canister 8 and the drawbar 136 is progressively loaded so as to be biased downwardly in the channel 50 in the second body section 32 of the housing 22. In this embodiment the lever arm 132 is configured to rotate until the longitudinal axis thereof is substantially parallel to the longitudinal axis of the elongate bar 164 of the support member 138, at which position the biasing element 134 is loaded with a predetermined actuation force which, through the drawbar 136, is applied to the base end II of the body 10 of the canister 8 which is held in position by the locking mechanism 16. When the locking mechanism 16 is released by a user inhaling through the mouthpiece 21, the body 10 of the canister 8 is free to be depressed and the force of the biasing element 134 acts on the drawbar 136 so as to cause the same to slide downwardly in the channel 50 in the second body section 32 towards the one end 52 thereof. This downward movement of the drawbar 136, through the projections 156, 156 on the elongate members 140, 140 thereof, causes the body 10 of the canister 8 to be depressed relative to the valve stem 13 thereof, which relative movement causes the actuation of the canister 8 so as to deliver a metered dose of medicament into the tubular section 20 defining in part the mouthpiece 21.

The casing 6 comprises a rear casing part 190 and a front casing part 192 which is pivotally coupled to the rear casing part 190. The rear casing part 190 is shaped and dimensioned to receive the delivery unit 4. In this embodiment the rear casing part 190 comprises opposed side wall members 194, 194 and lower, upper and rear wall members 198, 200, 202 which interconnect respectively the lower, upper and rear sections of the side wall members 194, 194. The side wall members 194, 194 of the rear casing part 190 each include a hook portion 204 at one, the upper, end 208 thereof behind which the respective opposed ends 155, 155 of the hinge pin 154 are located and a lug 212 at the other, lower end 216 thereof behind which the respective lateral projections 70, 70 on the housing 22 are clipped so as to secure the delivery unit 4 in the rear casing part 190. As will be appreciated, this configuration provides that the delivery unit 4 can be easily removed from and fitted to the casing 6 as would be necessary when replacing the canister 8. The lower wall member 198 of the rear casing part 190 includes a downwardly-directed and outwardly-biased projection 222 at one, the forward, end 223 thereof. The upper wall member 200 of the rear casing part 190 includes a lateral through hole 224 at one, the forward, end 225 thereof. In this embodiment the front casing part 192 comprises opposed side wall members 228, 228 and lower and front wall members 232, 234 which interconnect respectively the lower and front sections of the side wall members 228, 228. The side wall members 228, 228 and the lower wall member 232 of the front casing part 192 are configured so as to be a sliding fit about the side wall members 194, 194 and the lower wall member 198 of the rear casing part 190 such that the front casing part 192 can be telescoped about the rear casing part 190. The side wall members 228, 228 of the front casing part 192 further include opposed through holes 236, 236 at one, the upper, ends 238, 238 thereof, through which through holes 236, 236 and the through hole 224 in the upper wall member 200 of the rear casing part 190 extends a hinge pin 240 about which the casing parts 190, 192 are pivotally coupled. The lower wall member 232 of the front casing part 192 includes an enclosed elongate groove 241 in which the downwardly-directed projection 222 on the lower wall member 198 of the rear casing part 190 is normally captively disposed. The groove 241 includes a first, forward end wall 242 and a second, rear end wall 243, which end walls 242, 243 define limits to the normal relative movement of the casing parts 190, 192. In this embodiment the groove 241 includes a recess 244 adjacent the forward end wall 242 thereof for receiving the downwardly-directed projection 222 on the lower wall member 198 of the rear casing part 190 such as to latch the casing parts 190, 192 in the collapsed configuration, in which configuration the loading mechanism 18 is loaded. In operation, the downwardly-directed projection 222 on the lower wall member 198 of the rear casing part 190 is released from the recess 244 in the groove 241 by pulling on the front casing part 192; the casing 6 being opened completely by pulling on the front casing part 192 such that the downwardly-directed projection 222 on the lower wall member 198 of the rear casing part 190 is drawn out of the groove 241. The front wall member 234 of the front casing part 192 includes an inner surface 245 over which the free end 185 of the lever arm 132 of the loading mechanism 18 slides when the front casing part 192 is telescoped over the rear casing part 190 to rotate the lever arm 132. The front wall member 234 of the front casing part 192 further includes an opening 246 at one, the lower, end 248 thereof through which the mouthpiece 21 extends when the casing parts 190, 192 are telescoped together.

In use, a user takes the inhaler in one hand. In this embodiment the ergonomics of the design of the casing 6 are such that the user naturally locates the rear wall member 202 of the rear casing part 190 across the base of the fingers and acts on the front wall member 234 of the front casing part 192 just above the opening 246 therein to squeeze together the casing parts 190, 192. In this embodiment the distance between the point of force application on the front wall member 234 of the front casing part 192 and the pivot defined by the hinge pin 182 in the lever arm 132 is greater than the distance between the pivot defined by the hinge pin 154 about which the lever arm 132 rotates and the pivot defined by the hinge pin 182 in the lever arm 132 such that a mechanical advantage is achieved, thereby allowing a user to apply a lower force, albeit over a greater distance, to load the biasing element 134 than would be required if the force were applied directly to the biasing element 134. When the casing parts 190, 192 are telescoped together the canister 8 is loaded by the loading mechanism 18 and the mouthpiece 21 is exposed, in which position the casing parts 190, 192 are latched. The user then grips the mouthpiece 21 in the lips and inhales. When the user inhales, the vane 91 of the flap member 84 which is disposed in the tubular section 20 is drawn inwardly and the locking mechanism 16 released, thereby causing the body 10 of the canister 8 to be depressed relative to the valve stem 13 thereof by the stored force in the loading mechanism 18, which relative movement causes the actuation of the canister 8 so as to deliver a metered dose of medicament into the mouthpiece 21 which is inhaled by the user. The user then pulls on the front casing part 192 so as to release the latch between the casing parts 190, 192 and the front casing part 192 is returned under the action of the biasing element 134 to the expanded configuration; the biasing element 134 acting to rotate the free end 185 of the lever arm 132 upwardly and outwardly, which movement through the engagement with the inner surface 245 of the front wall member 234 of the front casing part 192 causes the front casing part 192 to return to the expanded configuration. In returning the casing parts 190, 192 to the expanded configuration the load is removed from the body 10 of the canister 8 and the body 10 of the canister 8 is driven upwardly relative to the valve stem 13 thereof under the action of the closure spring in the metering valve of the canister 8, which movement allows the locking mechanism 16 to reset to the locking position. In this position the inhaler is ready for re-use.

Finally, it will be understood that the present invention has been described in its preferred embodiment and can be modified in many different ways without departing from the scope of the appended claims.

What is claimed is:

1. An actuator for an inhaler for delivering medicament by inhalation, comprising:

a housing (22) which defines a cavity (34) for receiving a canister (8) which comprises a body (10) which defines a chamber containing medicament and a valve stem (13) which extends from the body (10), the body (10) and the valve stem (13) of the canister (8) when present being relatively movable between a first, non-actuated position in which the canister (8) is closed and a second, actuated position in which the canister (8) is open;

a nozzle block (24) for receiving the valve stem (13) of the canister (8);

a mouthpiece (21) for providing medicament from the nozzle block (24) to the mouth of a user;

a locking mechanism (16) for selectively locking the canister (8) in the non-actuated position, which locking mechanism (16) when released allows for the actuation of the canister (8); and a loading mechanism (18) which comprises a biasing element (134) for loading one of the body (10) or the valve stem (13) of the canister (8) with an actuating force for actuating the same connected to a lever arm (132) which is pivotally coupled by a pivot to the housing (22) for loading the biasing element (134) when rotated, which lever arm (132) is configured so as to be rotated in the one sense on the manual application of opposed forces substantially orthogonal to the longitudinal axis of the canister (8) said loading mechanism (18) further comprising a drawbar (136) which is movably disposed relative to the pivot of the lever arm (132) and coupled to the biasing element (134) such that the drawbar (136) is loaded as the biasing element (134) is loaded, which drawbar (136) includes at least one catch (156, 156) through which the biasing element (134) is coupled to one of the body (10) or the valve stem (13) of the canister (8) when present.

2. The actuator according to claim 1, wherein the biasing element (134) is coupled to the lever arm (132) at a point spaced from the pivot thereof.

3. The actuator according to claim 1, wherein the pivot of the lever arm (132) comprises a hinge pin (154) and the drawbar (136) includes at least one elongate slot (148) through which the hinge pin (154) extends such that the drawbar (136) is movably disposed to the housing (22) between a first position and a second, extended position.

4. The actuator according to claim 3, wherein the loading mechanism (18) further comprises a support member (138) which is pivotally coupled to the drawbar (136) and pivotally and slideably coupled to the lever arm (132) such that the drawbar (136) is moved to the extended position when the lever arm (132) is rotated in the other sense.

5. The actuator according to claim 4, wherein the drawbar (136) includes a projection (145) which is configured to engage the canister (8) when rotated in the other sense so as to draw the canister (8) at least partially from the cavity (34) defined by the housing (22).

6. The actuator according to claim 1, wherein the locking mechanism (16) comprises a movable flap member (84) which is configured to move on inhalation by a user through the mouthpiece (21) and a link assembly (86) which is operably coupled to the flap member (84) such as to be released from a locking position in which the canister (8) is locked in the non-actuated position on movement of the flap member (84).

7. The actuator according to claim 6, wherein the link assembly (86) comprises a first link (94) which is pivotally coupled to the housing (22) and includes an engagement surface (110) which, in the locking position, is configured to prevent relative movement of the body (10) and the valve stem (13) of the canister (8), a second link (96) which is pivotally coupled to the first link (94) and operably coupled to the flap member (84) and a biasing element (98) for biasing the first link (94) to the locking position.

8. The actuator according to claim 7, wherein, when the first link (94) is in the locking position, the engagement surface (10) of the first link (94) extends into the cavity (34) defined by the housing (22) such as to be engageable by the canister (8).

9. The actuator according to claim 7, wherein, when the first link (94) is in the locking position, the engagement surface (110) of the first link (94) extends substantially orthogonally to the longitudinal axis of the canister (8).

10. The actuator according to claim 7, wherein the first link (94) and the housing (22) are configured such that the first link (94) cannot be rotated beyond the locking position under the action of the biasing element (98).

11. The actuator according to claim 7, wherein the first link (94) further includes a further engagement surface (112) which is configured to engage a surface of the canister (8) when in the actuated position and hold the first link (94) in a displaced position.

12. The actuator according to claim 7, wherein the flap member (84) includes an axle (88) and the second link (96) includes a surface (128) which is configured to engage the axle (88) in the locking position and be disengaged therefrom on movement of the flap member (84) by inhalation.

13. The actuator according to claim 12, wherein the second link (96) includes an engagement surface (126) and the flap member (84) includes a lever member (92), which engagement surface (126) and lever member (92) are configured such that, on movement of the flap member (84) by inhalation, the lever member (92) engages the engagement surface (126) such as to move the second link (96) and disengage the catch surface (128) thereof from the axle (88) of the flap member (84).

14. The actuator according to claim 13, wherein the engagement surface (126) of the second link (96) and the lever member (92) are further configured such that the flap member (84) is disposed in the closed position when the locking mechanism (16) is in the locking position.

15. The actuator according to claim 13, wherein the second link (96) includes a further engagement surface (124) which together with the lever member (92) of the flap member (84) is configured to hold the flap member (84) in the open position when the locking assembly (16) is in the displaced position.

16. The actuator according to claim 1, further comprising a casing (6) which comprises first and second casing parts (190, 192) which are pivotally coupled between a first, closed position and a second, open position.

17. The actuator according to claim 16, wherein the housing (22) is fixed to one of the first and second casing parts (190, 192) and another of the first and second casing parts (190, 192) is configured, on movement of the first and second casing parts (190, 192) between the closed and open positions, to rotate the lever arm (132) such as to load the biasing element (134).

18. The actuator according to claim 17, wherein the other of the first and second casing parts (190, 192) includes an opening (246) through which the mouthpiece (21) extends in the open position of the casing parts (190, 192).

19. The actuator according to claim 16, wherein the casing (6) further comprises a latch for holding the casing parts (190, 192) in the open position.

20. The actuator according to claim 1, wherein the pivot of the lever arm (132) is substantially orthogonal to the longitudinal axis of the canister (8).

21. An inhaler comprising the actuator of claim 1 and a canister (8)s containing medicament.

* * * * *